US 8,559,716 B2

(12) United States Patent
Lukac

(10) Patent No.: US 8,559,716 B2
(45) Date of Patent: Oct. 15, 2013

(54) METHODS FOR SUPPRESSING STRUCTURED NOISE IN A DIGITAL IMAGE

(75) Inventor: Rastislav Lukac, San Jose, CA (US)

(73) Assignee: Foveon, Inc., Santa Clara, CA (US)

(*) Notice: Subject to any disclaimer, the term of this patent is extended or adjusted under 35 U.S.C. 154(b) by 52 days.

(21) Appl. No.: 13/466,405

(22) Filed: May 8, 2012

(65) Prior Publication Data

US 2012/0294525 A1 Nov. 22, 2012

Related U.S. Application Data

(60) Provisional application No. 61/487,959, filed on May 19, 2011.

(51) Int. Cl.
G06K 9/00 (2006.01)
(52) U.S. Cl.
USPC .......................................... 382/167
(58) Field of Classification Search
None
See application file for complete search history.

(56) References Cited

U.S. PATENT DOCUMENTS

| 5,606,375 A * | 2/1997 | Lee ............................... 348/606 |
| 6,335,990 B1 * | 1/2002 | Chen et al. .................... 382/261 |
| 6,907,144 B1 * | 6/2005 | Gindele ......................... 382/275 |
| 2003/0091243 A1 * | 5/2003 | Sasada .......................... 382/260 |
| 2006/0182364 A1 * | 8/2006 | John ............................. 382/260 |
| 2011/0123070 A1 * | 5/2011 | Sebok ........................... 382/106 |
| 2012/0093430 A1 * | 4/2012 | Sumi et al. .................... 382/252 |
| 2013/0128087 A1 * | 5/2013 | Georgiev et al. .............. 348/307 |

* cited by examiner

Primary Examiner — Barry Drennan
Assistant Examiner — Feng Niu
(74) Attorney, Agent, or Firm — Lewis and Roca LLP

(57) ABSTRACT

A method for suppressing structured noise in a digital image includes creating a smoothed version of the original image. Monotonic and slowly-varying image regions are detected by analyzing a residual image which is the function of the original image and its smoothed version. A local window is defined in each pixel location identified in the thresholding process as the location with structured noise and samples inside the window are randomly permuted to randomize the noise structures. A noise-filtered version of the original residual image is generated. The noise-filtered residual and the smoothed version of the original image are combined to produce a final image.

32 Claims, 5 Drawing Sheets

METHODS FOR SUPPRESSING STRUCTURED NOISE IN A DIGITAL IMAGE

CROSS-REFERENCE TO RELATED APPLICATIONS

This application claims the benefit of U.S. Provisional Patent Application Ser. No. 61/487,959, filed May 19, 2011, the entirety of which is incorporated by reference herein.

BACKGROUND

1. Field of the Invention

The present invention relates to processing of digital images. More particularly, the present invention relates to methods for suppressing structured noise such as row and column patterns in a digital image.

2. The Prior Art

Structured noise in digital images can have the form of row and column patterns, typically produced in a digital camera due to the sensor design (e.g., signal readout mode), or various other artifacts introduced to the image via image processing.

Row and column patterns are usually more obvious in images taken at higher ISO due to applying a gain to the image. Patterns are usually much more visible in images generated using refined processing aimed at high resolution output than images passed through aggressive denoising and JPEG compression. Therefore, software correction is needed to produce acceptable image quality in applications aimed at high resolution output. The problem is quite complex; the visibility of patterns usually varies with the scene content. In the present invention, row and column patterns (together with noise and edge/detail information) are extracted from the original image using a so-called residual signal. In one example, the residual signal is a three-channel color image. In another example, the residual signal is a one-channel image, allowing faster and simpler processing than detecting and correcting the patterns in RGB image data. Traditional filtering methods used to smooth the image reduce overall image sharpness and resolution of the residual image. Both of these effects are unacceptable.

The most common way of suppressing structured noise in digital images is to apply a smoothing technique, usually with a large spatial (two-dimensional) kernel. Unfortunately, such techniques tend to suppress desired image features such as edges and image details. Moreover, due to the required large spatial support it is also common that such techniques are slow, computationally complex, and have high memory requirements.

In the case of row and column patterns, it is also possible to use a smoothing solution which applies one-dimensional kernels in the direction orthogonal to the structure to be suppressed (i.e., row patterns are suppressed via smoothing in the vertical direction and column patterns suppressed via smoothing in the horizontal direction). However, such techniques often produce unsatisfactory results as they cannot fully remove structured noise and also tend to suppress the desired image features such as edges and image details. Therefore, a different approach is needed.

BRIEF DESCRIPTION

According to one aspect of the present invention, a method for suppressing structured noise in a digital image x includes creating a smoothed version x' of the image x. Monotonic and slowly-varying image regions are detected by analyzing a residual image z which is the function of the original image x and its smoothed version x'. A local window is defined in each pixel location identified in the thresholding process as the location with structured noise. Then, residual image samples inside the window are randomly permuted to randomize the noise structures, generating a noise-filtered version z' of the original residual image z. The noise-filtered residual z' and the smoothed image x' are combined to produce a final image y.

According to another aspect of the present invention, a one-dimensional window is defined in either the row or the column directions and residual image samples inside the window are randomly permuted to randomize the noise structures. Then, a one-dimensional window is defined in the other one of the row and column directions and residual image samples inside the window are randomly permuted to randomize the noise structures. Thus, a noise-filtered version z' of the original residual image z is generated. The noise-filtered residual z' and the smoothed image x' are combined to produce a final image y.

The method of the present invention analyzes residual signal statistics. Examples of such statistics include the local mean, median, maximum, minimum, and standard deviation. Then, the method creates the map to indicate desired edge content (no correction to be applied) and candidate regions for structured noise correction. Then, in candidate regions for correction, the present invention introduces spatial randomness to the residual image to preserve desired image edges while effectively removing structured noise.

According to one aspect of the present invention, a method for suppressing structured noise in a digital image x, comprises creating a smoothed version x' of the image x, then performing a thresholding process to detect monotonic and slowly-varying image regions by analyzing a residual image z which is the function of the original image x and its smoothed version x'. A one- or two-dimensional local window is defined in each pixel location identified in the thresholding process as the location with structured noise and residual image samples inside the window are randomly permuted to randomize the noise structures, generating a noise-filtered version z' of the original residual image z. A noise-filtered version z' of the residual image z is combined with the smoothed image x' to produce a final image y.

In some embodiments of the invention, the function of the original image x and its smoothed version x' is the difference between x and x'. In other embodiments, the function of the original image x and the smoothed version of the image x' is the ratio between x and x'.

In some embodiments of the invention, combining the noise-filtered residual z' and the smoothed image x' comprises adding the noise-filtered residual z' and the smoothed image x' for the original residual image obtained as z=x−x'. In other embodiments, combining the noise-filtered residual z' and the smoothed image x' comprises multiplying the noise-filtered residual z' and the smoothed image x' for the original residual image obtained as z=x/x'. The noise-filtered residual z' and the residual image z may be blended.

It should be understood that the function of the original image x and its smoothed version x' can also be defined as the difference between x' and x, or the ratio between x' and x. Such functions would imply that combining the noise-filtered residual z' and the smoothed image x' comprises subtracting the noise-filtered residual z' from the smoothed image x' for the original residual image obtained as z=x'−x, or dividing the smoothed image x' with the noise-filtered residual z' for the original residual image obtained as z=x'/x.

The smoothed version of the image x' may be created by applying low-pass filtering to the original image x. In some embodiments, such filtering can be accomplished by applying resizing methods to downsample an image and then to upsample a downsampled image in order to produce a smoothed image with dimensions identical to that of the original image. In other embodiments, the smoothed image x' can be created by applying at least one denoising or smoothing method to the original image x by applying at least one of spatial averaging, median, and wavelet-based filters to the original image x or by applying both resizing and smoothing operations to the original image x.

BRIEF DESCRIPTION OF THE DRAWING FIGURES

DETAILED DESCRIPTION

Figure 1:
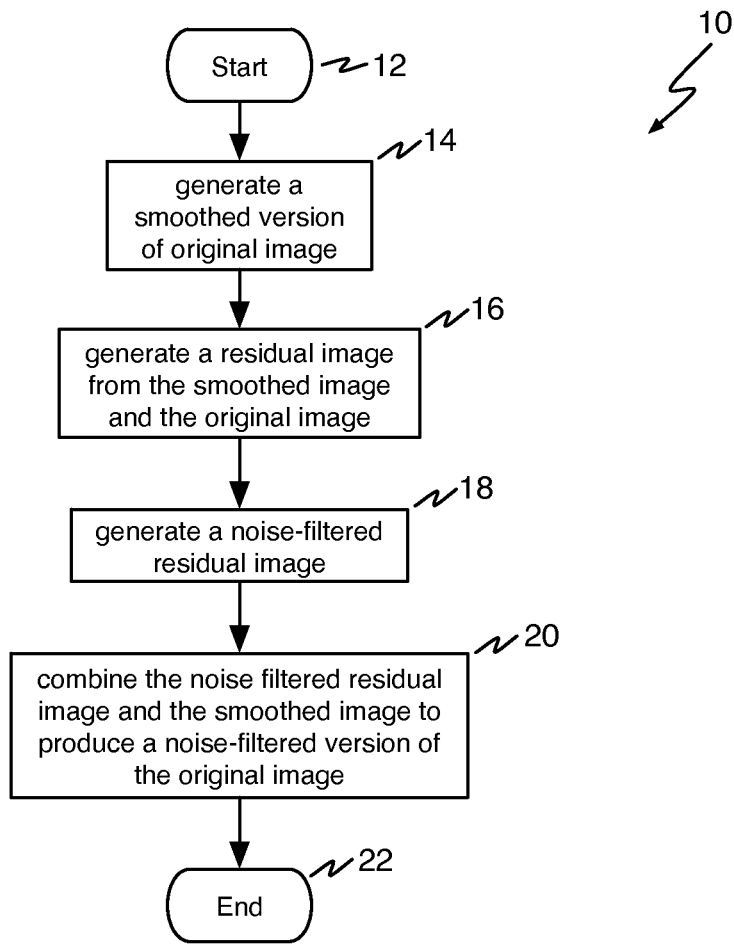
FIG. 1 is a flow diagram showing an illustrative embodiment of the present invention.

Persons of ordinary skill in the art will realize that the following description of the present invention is illustrative only and not in any way limiting. Other embodiments of the invention will readily suggest themselves to such skilled persons.

Methods are disclosed for suppressing structured noise such as row and column patterns in a digital image.

The present invention is characterized by localizing slowly varying image regions, spatially randomizing the high-frequency content of slowly varying image regions, blending of the original and noise-suppressed signals, and providing a trade-off between noise suppression and image-detail preservation.

A digital image x with R rows and S columns can be seen as a two-dimensional array of pixels $x_{(r,s)}$, where $r=1, 2, \ldots, R$ and $s=1, 2, \ldots, S$ denote the row and column coordinates, respectively. The image usually contains the desired high-frequency content such as edges, textures and fine details, as well as pixel noise and structured noise. The method of the present invention is employed to suppress the structured noise.

Since structured noise is usually visible in monotonic and slowly-varying image regions, the method of the present invention first detects such regions in order to subsequently suppress the noise. Depending on the application, the characteristics of the imaging device, image quality requirements, and/or user needs, the proposed method can complete the processing by applying an image blending process to preserve desired structures such as edges and image details.

Any edge detection or image segmentation solution can be used to analyze an image and detect the regions where structured noise may be visible. Since the present invention attacks the high-frequency component of slowly varying image regions, it analyzes the so-called residual image z which is the function of the original image x and its smoothed version x' created by applying the low-pass filtering technique(s) to the original image x. Examples of such low-pass filtering techniques include various resizing methods such as bilinear and bicubic interpolation which, typically, can be first used to downsample an image and then to upsample a downsampled image in order to produce a smoothed image with dimensions identical to that of the original image.

An alternative way is to use one or more smoothing methods, such as various spatial averaging, median, and wavelet-based filters. It is also possible to combine resizing and smoothing operations, for example, by performing first downsampling, then image smoothing, and then upsampling.

The residual image z expresses the similarity between x and x'. Using the additive formulation of the residual image, that is, $z=x-x'$, obtained as a difference between the original image x and its smoothed version x', or the inverse additive formulation $z=x'-x$, values of the image z close to zero indicate slowly-varying image regions and structured noise. Using the multiplicative formulation of the residual image, that is, $z=x/x'$, obtained as a ratio between the original image x and its smoothed version x', or the inverse multiplicative formulation $z=x'/x$, values close to one indicate slowly-varying image regions and structured noise. Thus, it is relatively easy to discriminate slowly-varying image regions from edges by simply thresholding the residual image.

In one example implementation, the thresholding process can be performed as $|z_{(r,s)}| \leq T$ where T is a tunable parameter. The value of T can be determined in the calibration according to certain numerical criterion (e.g., standard deviation, signal-to-noise ratio) or obtained through subjective evaluation of thresholding results. It is also possible to create an edge map with values equal to 1 indicating $|z_{(r,s)}| \leq T$ and values equal to 0 if the thresholding condition is not satisfied. The map can be further enhanced, for example, using various median filters or morphological filters to fill the holes and remove noise, or using various averaging filters for the purpose of blending the filtered residual with its original version. To eliminate the need of such enhancement, another solution is to identify the minimum $z_{(r,s)}^{min}$, and the maximum $z_{(r,s)}^{max}$ sample in a local neighborhood of and then perform thresholding of the value(s) produced as some function of $z_{(r,s)}^{min}$, and $z_{(r,s)}^{max}$, for example as $|z_{(r,s)}^{min}| \leq T$ and $|z_{(r,s)}^{max}| \leq T$ if $z=x-x'$ or $z=x'-x$, or as $|z_{(r,s)}^{min}-1| \leq T$ and $|z_{(r,s)}^{max}-1| \leq T$ if $z=x/x'$ or $z=x'/x$.

Once the regions with structured noise and undesired patterns are identified, the method of the present invention performs the noise suppression process. In one example, various low-pass filters can be applied to complete the noise suppression task. However, it can be generally observed that such filters usually have to operate in a very large neighborhood to produce satisfactory results, which may be too computationally expensive and memory consuming.

To avoid this drawback, the method of the present invention performs image randomization instead. Namely, a local window is placed in each pixel location identified in the thresholding process as the location with structured noise. Then $z_{(r,s)}$ samples inside the window are randomly permuted, thus randomizing the noise structures present in the residual image z.

In one example implementation, a two-dimensional window is used and the randomization procedure repeated until all pixel locations identified in the thresholding process are processed.

In another example implementation, a one-dimensional window is first applied in the horizontal (or vertical) direction and the randomization procedure is repeated until all pixel locations identified by thresholding are processed. Next, a one-dimensional window is applied in the vertical (or horizontal) direction and the randomization procedure is repeated until all pixel locations identified by thresholding are processed.

Performing the randomization procedure in all identified pixel locations completes the noise suppression process and generates the noise-filtered version z' of the original residual signal z. At this point it is possible to produce the final image y by adding the noise-filtered residual z' and the smoothed image x' for the additive formulation of the original residual image, that is, z=x-x', or by multiplying the noise-filtered residual z' and the smoothed image x' for the multiplicative formulation of the original residual image, that is, z=x/x'. Alternatively, the final image y can be produced by subtracting the noise-filtered residual z' from the smoothed image x' for the original residual image obtained as z=x'-x, or by dividing the smoothed image x' with the noise-filtered residual z' for the original residual image obtained as z=x'/x.

To control the amount of noise suppression during randomization, the method of the present invention allows for blending of the noise-filtered residual z' and its original version z. In the example implementation, the blending process can be formulated as $z''=\alpha z'+(1-\alpha)z$, where $\alpha$, usually between 0 and 1, is a tunable parameter, that can be selected, for example empirically by viewing test images or by optimizing the image smoothness in desired regions according to some predetermined criterion (e.g., standard deviation, signal-to-noise ratio). If $\alpha=0$, then no noise suppression is applied and the final residual image z'' is equivalent to the original residual image z. If $\alpha=1$, the final residual image z'' is equivalent to the noise-filtered residual z'. Once the blending operation is completed, the final image y is obtained by adding z'' and x' for the additive formulation of the original residual image, that is, z=x-x', or by multiplying z'' and x' for the multiplicative formulation of the original residual image, that is, z=x/x'. Alternatively, the final image y can be produced by subtracting z'' from x' for the original residual image obtained as z=x'-x, or by dividing x' with z'' for the original residual image obtained as z=x'/x.

In one example, the input image is directly passed through edge detection to localize the slowly varying image regions. The result of edge detection can be further refined or enhanced, for example, by applying techniques such as thresholding or spatial filtering. Then, detected slowly varying regions are processed in the noise suppression process (e.g., randomization, filtering, etc.). Finally, the image blending process can be applied to control the trade-off between noise suppression and image detail preservation.

In a more advanced example, the input image is first passed through low-pass filtering to create a smoothed version of the original image. Then, the residual image is created as the function (e.g., difference or ratio) of the original image and its smoothed version. Edge detection is then applied to the residual signal in order to localize the slowly varying image regions. The result of edge detection can be further refined or enhanced. Then, detected slowly varying regions are processed in the noise suppression process. Then, the image blending process can be applied to control the trade-off between noise suppression and image detail preservation in the residual image. The final residual image is combined (e.g., addition or multiplication, depending on the nature of the residual signal) with the smoothed version of the original image to produce the output image with suppressed structured noise.

Persons of ordinary skill in the art will recognize that, in the case of grayscale image, the application of the proposed solution is straightforward. In the case of color images, the proposed solution can be applied in each color channel separately, however, the randomization process can produce color artifacts. To avoid this drawback, the randomization process should apply the same permutation to all three color channels. This strategy is useful for randomizing directly the input image or the corresponding residual color signal.

A cost-effective implementation of the residual image processing can first create the grayscale version of the residual image by averaging (or combining in general) the color components of the residual image in each pixel location, then apply the edge detection, randomization, and blending processes to the grayscale residual image to produce the final residual image which is then combined with each color channel to produce the output image with suppressed structured noise. Alternatively, the grayscale version of the residual image can be created by relating (e.g., difference or ratio) the grayscale version of the input image and the grayscale version of the smoothed image. Such a grayscale version of a color image can be obtained by averaging (or combining in general) the color components of the image in each pixel location.

Referring now to FIG. 1, a flow diagram shows an illustrative method 10 according to one aspect of the present invention. The method starts at reference numeral 12.

At reference numeral 14, a smoothed image x' is generated from the original image x. At reference numeral 16, a residual image is generated as the function of the original image x and its smoothed version x'. The residual image may be subject to a thresholding or analysis process to detect monotonic and slowly-varying image regions.

At reference numeral 18, a noise-filtered version of the residual image is generated. A local window is defined in each pixel location identified in the thresholding process as the location with structured noise, residual image samples inside the window are randomly permuted to randomize the noise structures, and a noise-filtered version z' of the original residual image z is generated.

At reference numeral 20, the noise-filtered version of the residual image z' and the smoothed image x' are combined to produce a final image y. The process ends at referenced numeral 22.

Figure 2:
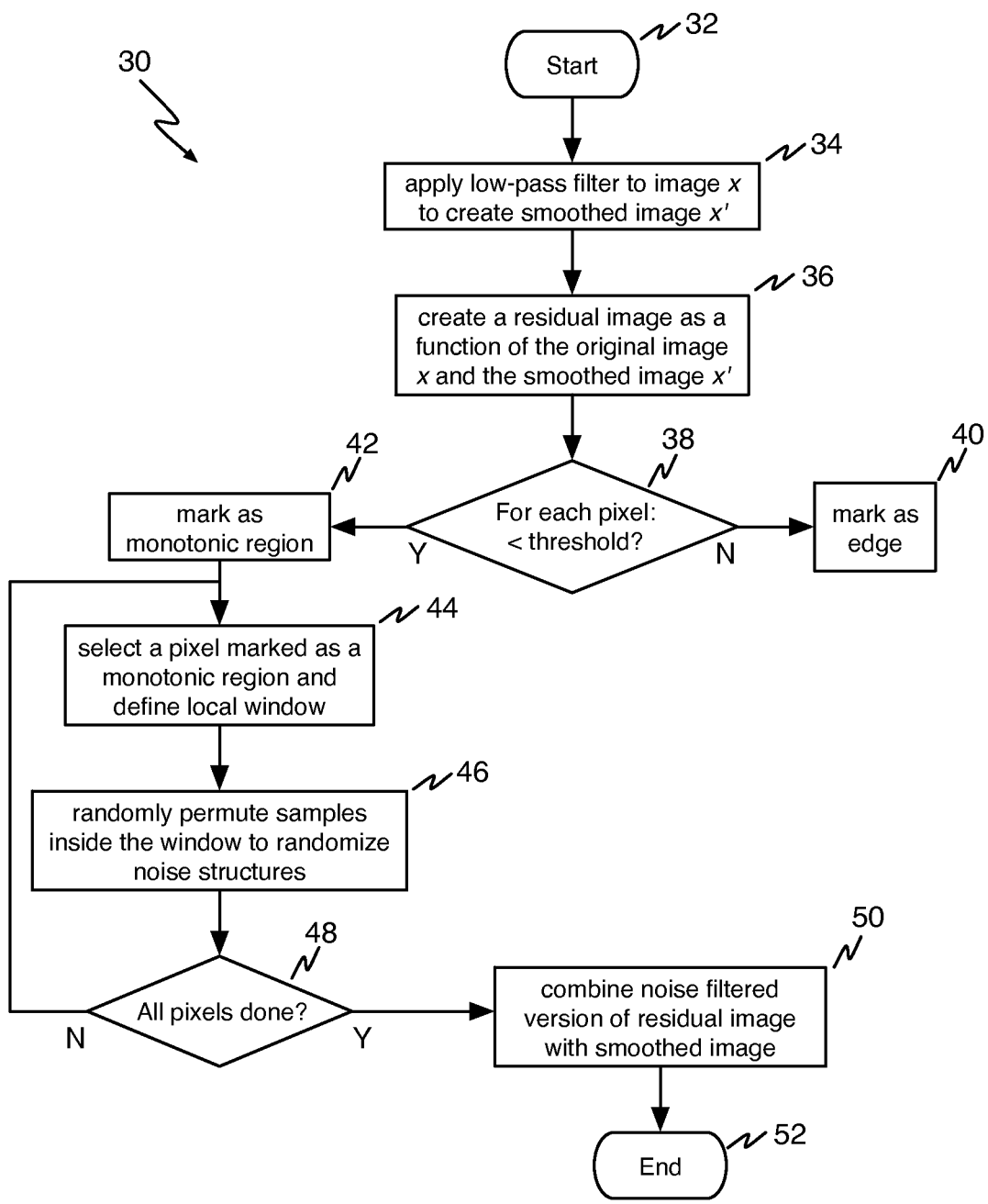
FIG. 2 is a flow diagram showing another illustrative embodiment of the present invention.

Referring now to FIG. 2, a flow diagram shows another illustrative method 30 according to one aspect of the present invention. The method starts at reference numeral 32.

At reference numeral 34, a smoothed version of the image x' is generated by applying low-pass filtering to the input image. At reference numeral 36, a residual image is generated as the function of the original image x and the smoothed image x', for example, using their ratio (for the multiplicative formulation of the residual signal) or difference (for the additive formulation of the residual signal). The residual image may be subject to a thresholding or analysis process at reference numerals 38, 40, and 42 to detect monotonic and slowly-varying image regions. For the additive formulation of the residual signal, any pixel having an absolute value above the threshold is marked at reference numeral 40 as an edge pixel and any pixel having an absolute value below the threshold is marked as being in a monotonic region at reference numeral 42. For the multiplicative formulation of the residual signal, any pixel having the absolute difference between one and the pixel value above the threshold is marked at reference numeral 40 as an edge pixel and any pixel having the absolute difference between one and the pixel value below the threshold is marked as being in a monotonic region at reference numeral 42.

At reference numeral 44, a pixel marked as being in a monotonic region is selected and a local window is defined in the neighborhood of that pixel. Examples of the local window include, but are not limited to, various square-shaped windows (e.g., 3×3, 5×5, etc.), rectangular-shaped windows, and circular-shaped windows. At reference numeral 46, samples inside the window are randomly permuted to randomize noise structures. At reference numeral 48 it is determined whether all pixels in monotonic regions have been processed.

If all pixels have not been processed, the process returns to reference numeral 44, where a pixel having marked as being in a monotonic region is selected and a local window is defined in the neighborhood of that pixel. If all pixels have been processed, a noise-filtered version of the residual image has been generated.

At reference numeral 50, the noise-filtered version of the residual image is combined with the smoothed image as previously disclosed herein. The process ends at reference numeral 52.

Figure 3:
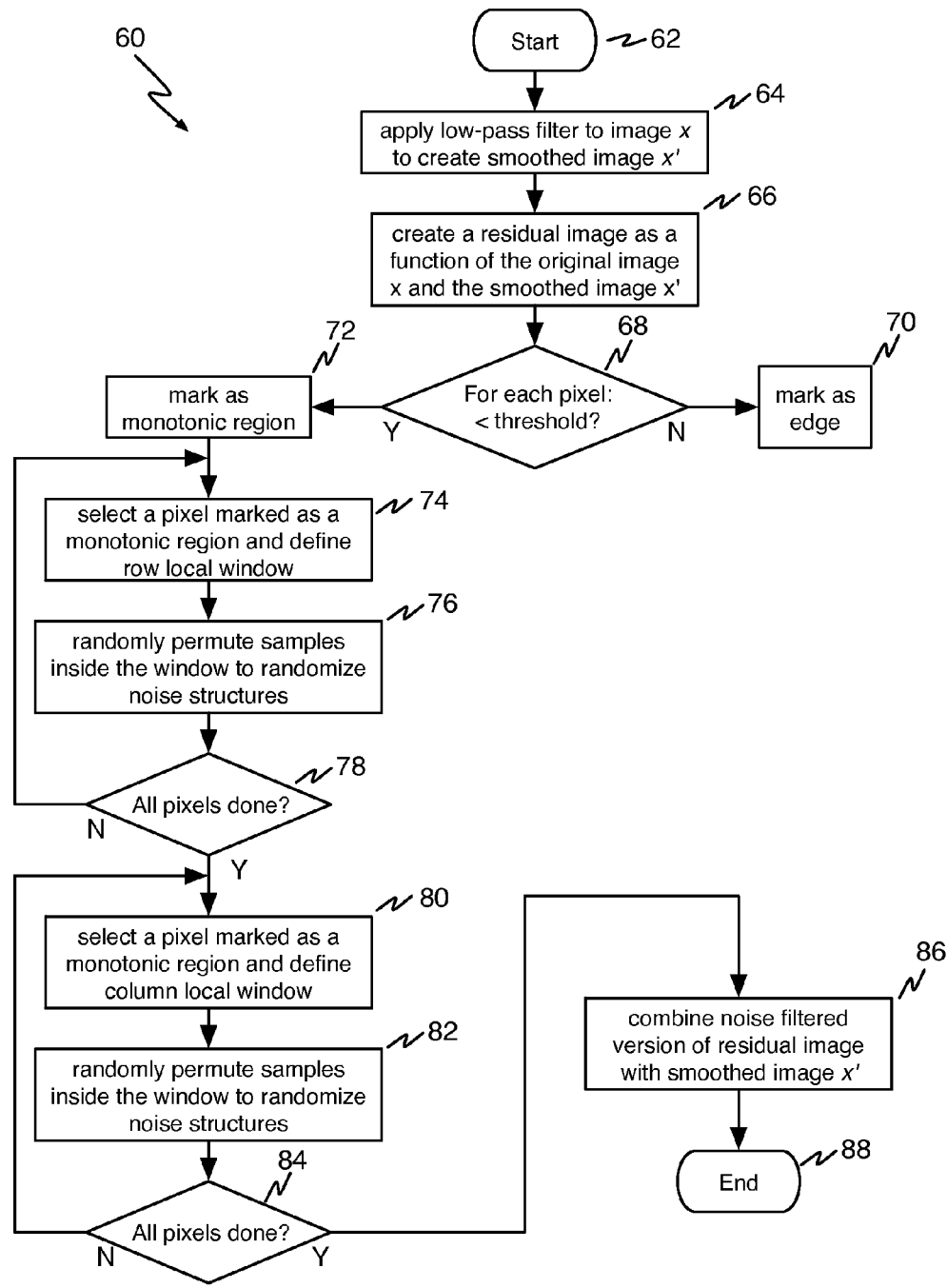
FIG. 3 is a flow diagram showing another illustrative embodiment of the present invention.

Referring now to FIG. 3, a flow diagram shows another illustrative method 60 according to one aspect of the present invention. In the illustrative embodiment shown in FIG. 3, the local window is determined in both row and column directions in the image.

At reference numeral 64, a smoothed version of the image x' is generated by applying low-pass filtering to the input image. At reference numeral 66, a residual image is generated from the original image and its smoothed version, for example, using their ratio (for the multiplicative formulation of the residual signal) or difference (for the additive formulation of the residual signal). The residual image may be subject to a thresholding process at reference numerals 68, 70, and 72 to detect monotonic and slowly-varying image regions by analyzing a residual image z which is the function of the original image x and its smoothed version x'. For the additive formulation of the residual signal, any pixel having an absolute value above the threshold is marked at reference numeral 70 as an edge pixel and any pixel having an absolute value below the threshold is marked as being in a monotonic region at reference numeral 72. For the multiplicative formulation of the residual signal, any pixel having the absolute difference between one and the pixel value above the threshold is marked at reference numeral 70 as an edge pixel and any pixel having the absolute difference between one and the pixel value below the threshold is marked as being in a monotonic region at reference numeral 72.

At reference numeral 74, a pixel marked as being in a monotonic region is selected and a local window is defined in a row direction in the neighborhood of that pixel. Example windows include, but are limited to, one-dimensional windows that span over three, five, seven, or nine neighboring samples and are centered in the pixel being filtered. At reference numeral 76, samples inside the row window are randomly permuted to randomize noise structures. At reference numeral 78 it is determined whether all pixels marked as being in a monotonic region have been processed.

If all pixels have not been processed, the process returns to reference numeral 74, where a pixel being marked as being in a monotonic region is selected and a local window is defined in the neighborhood of that pixel. If all pixels have been processed, the process proceeds to reference numeral 80 where a pixel marked as being in a monotonic region is selected and a local window is defined in a column direction in the neighborhood of that pixel. At reference numeral 82, samples inside the column window are randomly permuted to randomize noise structures. At reference numeral 84 it is determined whether all pixels marked as being in a monotonic region have been processed. If all pixels have been processed, a noise-filtered version of the residual image has been generated.

At reference numeral 86, the noise-filtered version of the residual image is combined with the smoothed image as previously disclosed herein. The process ends at reference numeral 88.

Figure 4:
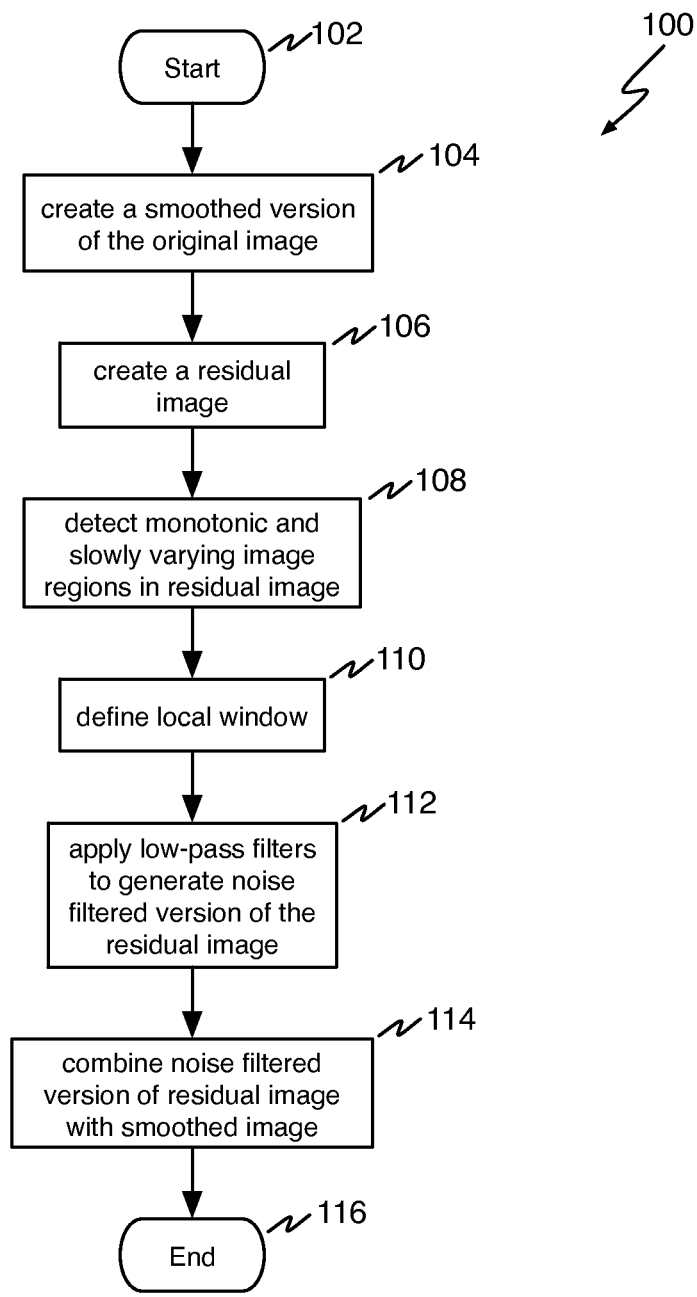
FIG. 4 is a flow diagram showing another illustrative embodiment of the present invention.

Referring now to FIG. 4, a flow diagram shows another illustrative method 100 according to one aspect of the present invention. In the illustrative embodiment shown in FIG. 4, low-pass filtering is performed within the local window. The method starts at reference numeral 102.

At reference numeral 104, a smoothed version of the original image is generated. At reference numeral 106, a residual image is generated from the smoothed image. The residual image may be subject to a thresholding process at reference numeral 108 to detect monotonic and slowly-varying image regions by analyzing a residual image which is the function of the original image and the smoothed version of the image. Any pixel that does not satisfy the predetermined thresholding condition is marked as an edge pixel; otherwise the pixels are marked as being in a monotonic region.

At reference numeral 110, a local window is defined in the neighborhood of each pixel marked as being in a monotonic region. At reference numeral 112, low-pass filtering is performed on pixels inside the window to generate a noise-filtered version of the residual image. At reference numeral 114, the noise-filtered version of the residual image and the smoothed image are combined to produce a final image. The process ends at referenced numeral 116.

Figure 5:
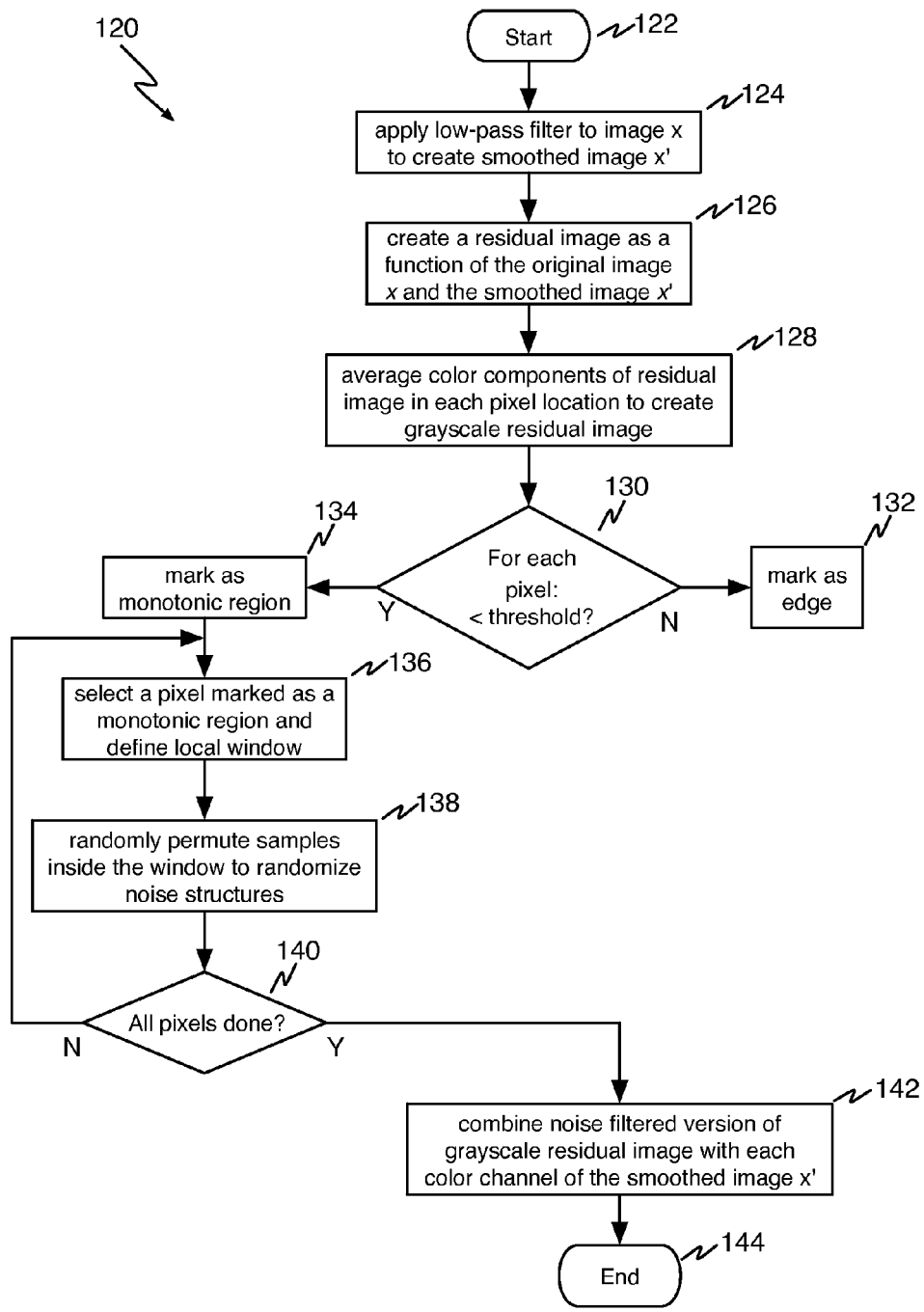
FIG. 5 is a flow diagram showing another illustrative embodiment of the present invention.

Referring now to FIG. 5, a flow diagram shows another illustrative method 120 according to one aspect of the present invention. In the illustrative embodiment shown in FIG. 5, an illustrative method for processing color images is shown. The method starts at reference numeral 122.

At reference numeral 124, a smoothed version of the image x' is generated by applying low-pass filtering to the input image x. At reference numeral 126, a residual image is generated from the original image x and its smoothed version x', for example, using their ratio (for the multiplicative formulation of the residual signal) or difference (for the additive formulation of the residual signal). At reference numeral 128, the color components of the residual image are averaged in each pixel location to create a grayscale residual image.

At reference numerals 130, 132, and 134, monotonic and slowly-varying image regions are detected by analyzing a grayscale version of the residual image z. For the additive formulation of the residual signal, any pixel having an absolute value of the grayscale version of the residual image z above the threshold is marked at reference numeral 132 as an edge pixel and any pixel having an absolute value of the grayscale version of the residual image z below the threshold is marked as being in a monotonic region at reference numeral 134. For the multiplicative formulation of the residual signal, any pixel having the absolute difference between one and the pixel value of the grayscale version of the residual image z above the threshold is marked at reference numeral 132 as an edge pixel and any pixel having the absolute difference between one and the pixel value of the grayscale version of the residual image z below the threshold is marked as being in a monotonic region at reference numeral 134.

At reference numeral 136, a pixel marked as being in a monotonic region is selected and a local window is defined in the neighborhood of that pixel. Examples of the local window include, but are not limited to, various square-shaped windows (e.g., 3×3, 5×5, etc.), rectangular-shaped windows, and circular-shaped windows. At reference numeral 138, samples inside the window are randomly permuted to randomize noise structures. At reference numeral 140 it is determined whether all pixels marked as being in a monotonic region have been processed.

If all pixels have not been processed, the process returns to reference numeral 136, where a pixel having a value below the threshold is selected and a local window is defined in the neighborhood of that pixel. If all pixels have been processed, a noise-filtered version of the grayscale residual image has been generated.

At reference numeral 142, the noise-filtered version of the grayscale residual image is combined with the smoothed image as previously disclosed herein. The process ends at reference numeral 144.

It should be appreciated that in the foregoing description of exemplary embodiments of the invention, various features of the invention are sometimes grouped together in a single embodiment, figure, or description thereof for the purpose of streamlining the disclosure and aiding in the understanding of one or more of the various inventive aspects. Inventive aspects lie in less than all features of a single foregoing disclosed embodiment, and each embodiment described herein may contain more than one inventive feature.

While embodiments and applications of this invention have been shown and described, it would be apparent to those skilled in the art that many more modifications than mentioned above are possible without departing from the inventive concepts herein. The invention, therefore, is not to be restricted except in the spirit of the appended claims.

What is claimed is:

1. A method for suppressing structured noise in an original image, comprising:
   generating a smoothed version of the original image;
   generating a residual image from the original image and the smoothed version of the original image;
   detecting monotonic and slowly-varying image regions by analyzing the residual image;
   defining a local window in each pixel location identified in a thresholding process as being in the monotonic and slowly-varying image regions;
   randomly permuting residual image samples inside the window to randomize the noise structures, thus generating a noise-filtered version of the residual image; and
   combining the smoothed image and the noise-filtered version of the residual image to produce a final image.

2. The method of claim 1 wherein the function of the original image and the smoothed version of the original image is the difference between the original image and the smoothed version of the original image.

3. The method of claim 1 wherein the function of the original image and the smoothed version of the original image is the ratio between the original image and the smoothed version of the original image.

4. The method of claim 1 wherein the function of the original image and the smoothed version of the original image is the difference between the smoothed version of the original image and the original image.

5. The method of claim 1 wherein the function of the original image and the smoothed version of the original image is the ratio between the smoothed version of the original image and the original image.

6. The method of claim 1 wherein combining the noise-filtered residual image and the smoothed version of the original image comprises adding the noise-filtered residual image and the smoothed version of the original image.

7. The method of claim 1 wherein combining the noise-filtered residual image and the smoothed version of the original image comprises multiplying the noise-filtered residual image and the smoothed version of the original image.

8. The method of claim 1 wherein combining the noise-filtered residual image and the smoothed version of the original image comprises subtracting the noise-filtered residual image from the smoothed version of the original image.

9. The method of claim 1 wherein combining the noise-filtered residual image and the smoothed version of the original image comprises dividing the smoothed version of the original image with the noise-filtered residual image.

10. The method of claim 1, further including blending the noise-filtered residual image and the residual image.

11. The method of claim 10 wherein blending the noise-filtered residual image and the residual image comprises:
    generating a final residual image as a weighted average of the residual image and the noise-filtered residual image; and
    generating a final image by combining the final residual image and the smoothed version of the original image.

12. The method of claim 11 wherein combining the final noise-filtered residual image and the smoothed version of the original image comprises adding the final noise-filtered residual image and the smoothed version of the original image.

13. The method of claim 11 wherein combining the final noise-filtered residual image and the smoothed version of the original image comprises multiplying the final noise-filtered residual image and the smoothed version of the original image.

14. The method of claim 11 wherein combining the final noise-filtered residual image and the smoothed version of the original image comprises subtracting the final noise-filtered residual image from the smoothed version of the original image.

15. The method of claim 11 wherein combining the final noise-filtered residual image and the smoothed version of the original image comprises dividing the smoothed version of the original image with the final noise-filtered residual image.

16. The method of claim 1 wherein the smoothed version of the original image is created by applying low-pass filtering to the original image.

17. The method of claim 16 wherein applying low-pass filtering to the original image comprises applying resizing methods to downsample the image and then to upsample the downsampled image in order to produce a smoothed image with dimensions identical to that of the original image.

18. The method of claim 17 wherein applying resizing methods comprises applying one of bilinear and bicubic interpolation to the original image.

19. The method of claim 1 wherein the smoothed version of the original image is created by applying at least one denoising method to the original image.

20. The method of claim 19 wherein applying at least one denoising or smoothing method to the original image comprises applying at least one of spatial averaging, median, and wavelet-based filters to the original image.

21. The method of claim 1 wherein the smoothed version of the image is created by applying both resizing and denoising operations to the original image.

22. The method of claim 21 wherein applying both resizing and denoising operations to the original image comprises performing first downsampling, then denoising, and then upsampling operations to the original image.

23. The method of claim 1 wherein defining a local window in each pixel location identified in the thresholding process as the location with structured noise comprises defining a two-dimensional window.

24. The method of claim 1 wherein defining a local window in each pixel location identified in the thresholding process as the location with structured noise comprises defining a one-dimensional window, for example, in either the row or column direction or in either of the two diagonal directions.

25. A method for suppressing structured noise in a digital image, comprising:
   creating a smoothed version of the original image;
   detecting monotonic and slowly-varying image regions by analyzing a residual image which is the function of the original image and its smoothed version;
   defining a first one-dimensional window;
   in each pixel location inside the region identified in a thresholding process as being in the monotonic and slowly-varying image regions with structured noise, randomly permuting samples inside the first one-dimensional window to randomize the noise structures;
   defining a second one-dimensional window;
   in each pixel location inside the region identified in the thresholding process as being in the monotonic and slowly-varying image regions with structured noise, randomly permuting samples inside the second one-dimensional window to randomize the noise structures;
   combining the noise-filtered (randomized) residual and the smoothed version of the original image to produce a final image.

26. The method of claim 25 wherein defining the second window comprises of defining the window the direction orthogonal to the direction of the first window.

27. The method of claim 25 wherein combining the noise-filtered residual and the smoothed version of the original image comprises adding the noise-filtered residual and the smoothed version of the original image for the original residual image obtained as the difference between the original image and its smoothed version.

28. The method of claim 25 wherein combining the noise-filtered residual and the smoothed version of the original image comprises multiplying the noise-filtered residual and the smoothed version of the original image for the original residual image obtained as the ratio of the original image and its smoothed version.

29. The method of claim 25 wherein combining the noise-filtered residual and the smoothed version of the original image comprises dividing the smoothed version of the original image with the noise-filtered residual image for the original residual image obtained as the ratio of the smoothed version of the original image and the original image.

30. The method of claim 25 wherein combining the noise-filtered residual and the smoothed version of the original image comprises subtracting the noise-filtered residual image from the smoothed version of the original image for the original residual image obtained as the difference between the smoothed version of the original image and the original image.

31. A method for suppressing structured noise in a digital color image, comprising:
   generating a smoothed version of the image;
   generating a residual image from the original image and its smoothed version;
   generating a grayscale residual image by averaging the color components of the residual image in each pixel location to create a grayscale residual image;
   detecting monotonic and slowly-varying image regions by analyzing the residual image;
   defining a local window in each pixel location identified in a thresholding process as being in a monotonic and slowly-varying image region;
   randomly permuting residual image samples inside the window to randomize the noise structures;
   generating a noise-filtered version of the grayscale residual image;
   combining the noise-filtered version of the grayscale residual image and each color channel of the smoothed image to produce a final color image.

32. A method for suppressing structured noise in a digital color image, comprising:
   generating a grayscale version of the original color image;
   generating a smoothed version of the original color image;
   generating a grayscale version of the smoothed color image;
   generating a residual image from the grayscale version of the original image and grayscale version of the smoothed color image;
   detecting monotonic and slowly-varying image regions by analyzing the residual image;
   defining a local window in each pixel location identified in a thresholding process as being in a monotonic and slowly-varying image regions;
   randomly permuting residual image samples inside the window to randomize the noise structures;
   generating a noise-filtered version of the residual image;
   combining the noise-filtered version of the residual image and each color channel of the smoothed image to produce a final color image.

* * * * *